United States Patent
Ito et al.

(10) Patent No.: US 10,031,068 B2
(45) Date of Patent: Jul. 24, 2018

(54) STEEL SHEET INSPECTION DEVICE, STEEL SHEET INSPECTION METHOD, AND STEEL SHEET MANUFACTURING METHOD

(71) Applicant: JFE STEEL CORPORATION, Tokyo (JP)

(72) Inventors: Tomohiko Ito, Tokyo (JP); Junichi Yotsuji, Tokyo (JP); Shigehiro Takajo, Tokyo (JP); Hiroi Yamaguchi, Tokyo (JP); Kazuhiro Hanazawa, Tokyo (JP); Yasunari Koga, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 485 days.

(21) Appl. No.: 14/425,983

(22) PCT Filed: Sep. 25, 2013

(86) PCT No.: PCT/JP2013/075944
§ 371 (c)(1),
(2) Date: Mar. 4, 2015

(87) PCT Pub. No.: WO2014/050907
PCT Pub. Date: Apr. 3, 2014

(65) Prior Publication Data
US 2015/0253242 A1    Sep. 10, 2015

(30) Foreign Application Priority Data

Sep. 28, 2012   (JP) .................................. 2012-216379

(51) Int. Cl.
*H01F 1/16*      (2006.01)
*C21D 8/12*      (2006.01)
(Continued)

(52) U.S. Cl.
CPC .............. *G01N 21/21* (2013.01); *C21D 1/38* (2013.01); *C21D 8/1244* (2013.01);
(Continued)

(58) Field of Classification Search
None
See application file for complete search history.

(56) References Cited

U.S. PATENT DOCUMENTS 3,663,108 A * 5/1972 Yamamuro .............. G01B 7/02
                                                           356/429
6,359,686 B1 * 3/2002 Ariglio .............. G01N 21/8901
                                                           356/239.1
(Continued)

FOREIGN PATENT DOCUMENTS

EP      0 331 497 A2    9/1989
JP      S59180355 A    10/1984
(Continued)

OTHER PUBLICATIONS

Machine translation of JP2012031519, generated via Espacenet Oct. 31, 2017, pp. 1-13.*

(Continued)

*Primary Examiner* — Colleen P Dunn
(74) *Attorney, Agent, or Firm* — Oliff PLC (57) ABSTRACT

A steel sheet inspection device includes: a magnetooptic element that is able to detect, as an optical property, a magnetic domain structure of a steel sheet to be inspected; a light source that irradiates the magnetooptic element with linearly polarized light; a detector that detects the linearly polarized light with a polarization plane rotated according to the magnetic domain structure of the steel sheet transferred to the magnetooptic element; and a drive mechanism that
(Continued)

drives at least the magnetooptic element so as to contact and separate the steel sheet and the magnetooptic element with and from each other.

20 Claims, 7 Drawing Sheets (51) Int. Cl.
*G01N 21/21* (2006.01)
*G01R 33/032* (2006.01)
*G01N 21/86* (2006.01)
*C22C 38/00* (2006.01)
*H01F 41/02* (2006.01)
*C21D 11/00* (2006.01)
*C21D 1/38* (2006.01)
*G01N 27/82* (2006.01)
*C21D 1/34* (2006.01)
*C21D 9/46* (2006.01)

(52) U.S. Cl.
CPC ............ *C21D 8/1294* (2013.01); *C21D 11/00* (2013.01); *C22C 38/00* (2013.01); *G01N 21/86* (2013.01); *G01R 33/032* (2013.01); *H01F 1/16* (2013.01); *H01F 41/02* (2013.01); *C21D 1/34* (2013.01); *C21D 8/12* (2013.01); *C21D 9/46* (2013.01); *G01N 27/82* (2013.01); *G01N 2021/8609* (2013.01)

(56) References Cited

U.S. PATENT DOCUMENTS

| | | | |
|---|---|---|---|
| 6,934,068 | B2 | 8/2005 | Kochergin |
| 2004/0218249 | A1* | 11/2004 | Kochergin ................ G02F 1/09 359/280 |
| 2013/0130043 | A1 | 5/2013 | Omura et al. |

FOREIGN PATENT DOCUMENTS

| | | | |
|---|---|---|---|
| JP | S62102103 | A | 5/1987 |
| JP | S62115357 | A | 5/1987 |
| JP | H05119130 | A | 5/1993 |
| JP | H11-293416 | A | 10/1999 |
| JP | 2002257718 | A | 9/2002 |
| JP | 2007101519 | A | 4/2007 |
| JP | 2012031519 | * | 2/2012 |
| JP | 2012031519 | A | 2/2012 |
| JP | 2012-047645 | A | 3/2012 |
| JP | 2012052230 | A | 3/2012 |

OTHER PUBLICATIONS

Feb. 19, 2016 Office Action issued in Korean Patent Application No. 10-2015-7005763.
Dec. 2, 2016 Office Action issued in Chinese Patent Application No. 201380050432.7.
Dec. 3, 2013 International Search Report issued in International Application No. PCT/JP2013/075944.
Jul. 18, 2016 Extended European Search Report issued in European Patent Application No. 13841923.9.
Vasiliev, Mikhail et al., "Magnetic Field Sensors and Visualizers Using Magnetic Photonic Crystals", Optical Sensing II, Apr. 14, 2008, vol. 7004, XP055285280, pp. 70045D-1-70045D-4.

* cited by examiner

STEEL SHEET INSPECTION DEVICE, STEEL SHEET INSPECTION METHOD, AND STEEL SHEET MANUFACTURING METHOD

FIELD

The present invention relates to a steel sheet inspection device, a steel sheet inspection method, and a steel sheet manufacturing method.

BACKGROUND

Electrical steel sheets are steel sheets having excellent magnetic properties with high magnetic permeability and small core loss. For example, grain oriented electrical steel sheets are often used in cores of transformers. Alternating current flowing through an electric wire wound around a core of a transformer generates an alternating magnetic field inside the core. In general, if an alternating magnetic field is applied in a steel sheet, eddy current loss and hysteresis loss are generated. Electrical steel sheets are demanded to have such eddy current loss and hysteresis loss reduced therein.

The generation of eddy current loss upon the application of an alternating magnetic field inside a steel sheet is unavoidable, and the greater the frequency is, the greater the eddy current loss will be. A width of a magnetic domain of a steel sheet is one factor influencing this eddy current loss, and the narrower this width is, the more the eddy current loss is able to be reduced. Thus, magnetic properties of a steel sheet and a shape of the magnetic domain are known to be very deeply related to each other.

Accordingly, in a manufacturing process of grain oriented electrical steel sheets, in order to reduce the eddy current loss, a method of refining magnetic domains (magnetic domain refining process) is performed. A magnetic domain of a grain oriented electrical steel sheet extends in a rolling direction, and by adding a strain or forming a groove in a direction intersecting this magnetic domain, the magnetic domain is able to be refined. A method of giving a thermal strain by irradiation with laser, electron beams, or the like, in the direction intersecting the magnetic domain, is known as a method of adding the strain. An inspection technique is known, which is for observing a magnetic domain structure, such as a shape of a magnetic domain, in order to inspect whether or not this magnetic domain refining process has been performed appropriately (see Patent Literature 1 and Patent Literature 2).

CITATION LIST

Patent Literature

Patent Literature 1: Japanese Patent Application Laid-open No. 2007-101519
Patent Literature 2: Japanese Patent Application Laid-open No. 2002-257718

SUMMARY

Technical Problem

However, by conventional inspection techniques, a magnetic domain structure of a steel sheet subjected to the magnetic domain refining process is not able to be detected immediately after the magnetic domain refining process and the steel sheet needs to be separately sampled for inspection offline. For example, in the inspection technique described in Patent Literature 1, time is needed for the magnetic powder to move through the solution and form an image reflecting the magnetic domain structure. Therefore, the yield is reduced due to nonconforming products being continuously manufactured even if a problem occurs in the magnetic domain refining process. Further, the inspection technique described in Patent Literature 2 utilizes a magnetooptic effect, and since a light beam spot is formed and this light beam spot is one-dimensionally or two dimensionally scanned to inspect a magnetic domain, for inspection on a manufacturing line, a long period of inspection time is required.

The present invention has been made in view of the above, and an object thereof is to provide a steel sheet inspection device, a steel sheet inspection method, and a steel sheet manufacturing method, which are able to improve the yield by visualizing and inspecting a magnetic domain structure of a steel sheet immediately after a magnetic domain refining process.

Solution to Problem

To solve the above-described problem and achieve the object, a steel sheet inspection device according to the present invention includes: a magnetooptic element that is able to detect, as an optical property, a magnetic domain structure of a steel sheet to be inspected; a light source that irradiates the magnetooptic element with linearly polarized light; a detector that detects the linearly polarized light with a polarization plane rotated according to the magnetic domain structure of the steel sheet transferred to the magnetooptic element; and a drive mechanism that drives at least the magnetooptic element so as to contact and separate the steel sheet and the magnetooptic element with and from each other.

To solve the above-described problem and achieve the object, a steel sheet inspection method according to the present invention includes: a contacting step of contacting, with a steel sheet to be inspected, a magnetooptic element that is able to detect, as an optical property, a magnetic domain structure of the steel sheet; an irradiating step of irradiating the magnetooptic element with linearly polarized light; a detecting step of detecting a rotation of a polarization plane of the linearly polarized light reflected by the magnetooptic element; a measuring step of measuring the magnetic domain structure of the steel sheet from the rotation of the polarization plane; and a separating step of separating the magnetooptic element from the steel sheet.

To solve the above-described problem and achieve the object, a steel sheet manufacturing method according to the present invention includes: a magnetic domain refining step of irradiating a surface of a steel sheet with an electron beam or laser; a contacting step of contacting a magnetooptic element that is able to detect, as an optical property, a magnetic domain structure of a steel sheet, with a region on the steel sheet, the region having been irradiated with the electron beam or laser; an irradiating step of irradiating the magnetooptic element with linearly polarized light; a detecting step of detecting a rotation of a polarization plane of the linearly polarized light reflected by the magnetooptic element; an extracting step of extracting a magnetic domain discontinuity formed by the irradiation with the electron beam or laser; a width evaluating step of evaluating an average width of the magnetic domain discontinuity; and an output adjusting step of increasing or decreasing an output of the electron beam or laser based on the evaluation by the width evaluating step.

Advantageous Effects of Invention

A steel sheet inspection device, a steel sheet inspection method, and a steel sheet manufacturing method according to the present invention achieve an effect of being able to improve the yield by visualizing and inspecting a magnetic domain structure of a steel sheet immediately after a magnetic domain refining process.

DESCRIPTION OF EMBODIMENTS

Hereinafter, a steel sheet inspection device, a steel sheet inspection method, and a steel sheet manufacturing method according to an embodiment of the present invention will be described in detail based on the drawings. The present invention is not limited by the embodiment described below.

[Steel Sheet Inspection Device]

Figure 1:
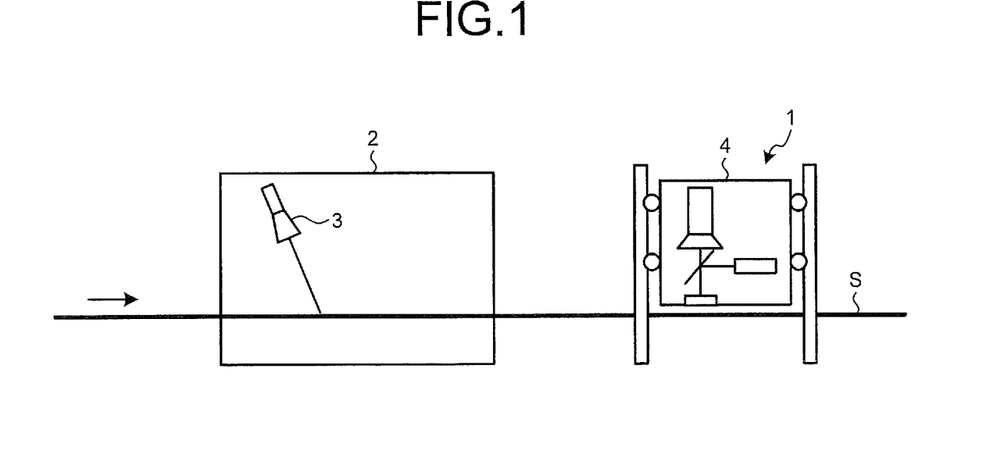
FIG. 1 is a manufacturing line configuration diagram illustrating an arrangement of a steel sheet inspection device according to an embodiment of the present invention.

FIG. 1 is a manufacturing line configuration diagram illustrating an arrangement of a steel sheet inspection device 1 according to the embodiment of the present invention. As illustrated in FIG. 1, the steel sheet inspection device 1 according to the embodiment of the present invention is arranged at a rear stage of a magnetic domain refining device 2 that performs a magnetic domain refining process on a steel sheet "S". The magnetic domain refining device 2 includes electron guns 3 therein, and is a device that gives a thermal strain in a direction intersecting a magnetic domain of the steel sheet "S" by irradiating the steel sheet "S" with electron beams from the electron guns 3.

The steel sheet inspection device 1 is a device that contacts the steel sheet "S" and inspects a magnetic domain structure of the steel sheet "S" by an inspection unit 4 being driven when the manufacturing line is temporarily stopped. Hereinafter, with reference to FIG. 2 to FIG. 5, an example of a configuration of the steel sheet inspection device 1 will be described.

Figure 2:
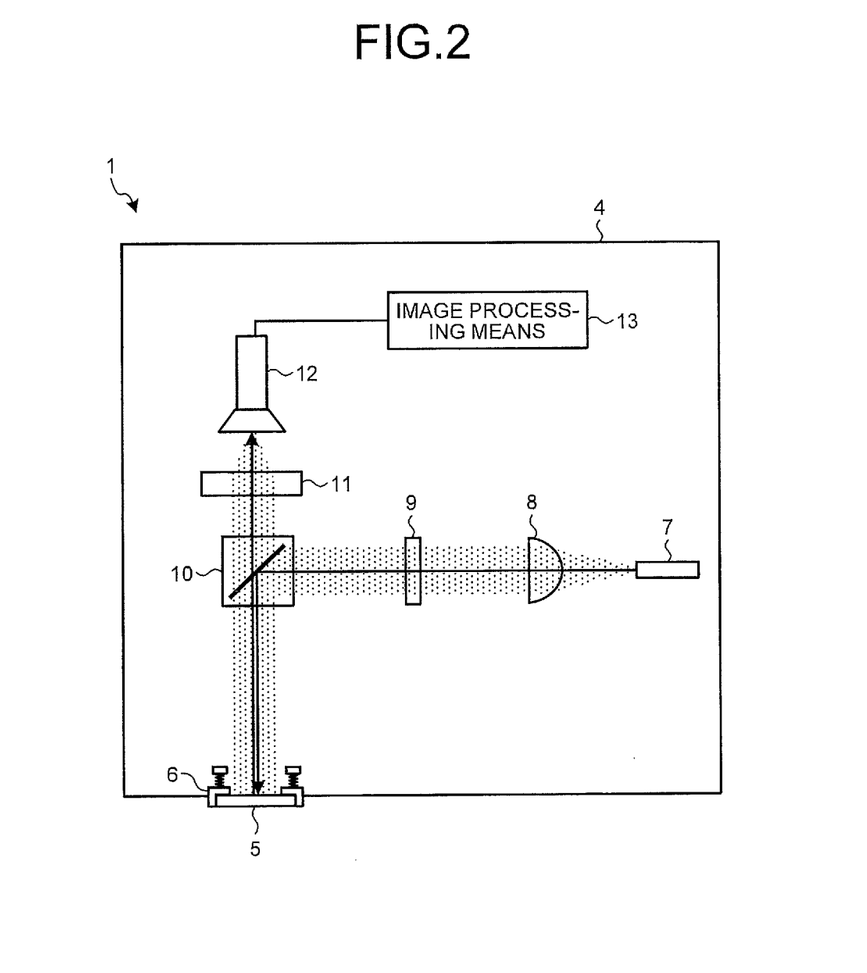
FIG. 2 is a schematic diagram illustrating an example of an internal configuration of an inspection unit of the steel sheet inspection device.

FIG. 2 is a schematic diagram illustrating an example of an internal configuration of the inspection unit 4 of the steel sheet inspection device 1. As illustrated in FIG. 2, the inspection unit 4 includes a magnetooptic element 5 that converts the magnetic domain structure of the steel sheet "S" to an optical property, a holder 6 that fixes the magnetooptic element 5 to the inspection unit 4 via an elastic body, and an incident-light optical system that irradiates the magnetooptic element 5 with linearly polarized light and detects reflected polarized light reflected from the magnetooptic element 5. Specifically, the inspection unit 4 includes, as the incident-light optical system, a light source 7, a collimator lens 8, a polarizer (polarizing filter) 9, a half mirror 10, an analyzer (polarizing filter) 11, and a detector 12.

The magnetooptic element 5 is an element that converts the magnetic domain structure of the steel sheet "S" to the optical property by a magnetooptic effect called Faraday effect. Faraday effect is an effect of a polarization plane rotating by a magnetic field felt by a substance when linearly polarized light is transmitted through the substance, and magnetic garnet is a representative substance achieving this Faraday effect.

By the inspection unit 4 being driven, the magnetooptic element 5 comes into contact with the steel sheet "S", the magnetic domain structure of the steel sheet "S" is transferred to the magnetooptic element 5, and the polarization plane of the polarized light, with which the magnetooptic element 5 is irradiated, rotates. The holder 6 fixes the magnetooptic element 5 to the inspection unit 4 via the elastic body in order to relieve the impact when the inspection unit 4 is driven to contact the magnetooptic element 5 with the steel sheet "S".

The light source 7 is for irradiating the magnetooptic element 5 with linearly polarized light, and for example, a general light source, such as a semiconductor laser light source or an LED light source, is used. The light source 7 does not need to be a light source that emits polarized light directly, and generates, in combination with the polarizer (polarizing filter) 9, linearly polarized light, with which the magnetooptic element 5 is irradiated. Further, the light source 7 is used in combination with an optical element, such as the collimator lens 8, so as to be able to emit polarized light as parallel light.

The polarizer 9 is a polarizing filter that converts light rays emitted from the light source 7 to linearly polarized light. The polarizer 9 adjusts polarized light detected by the detector 12, by adjusting a relative angle thereof with the analyzer 11. That is, the polarizer 9 has a rotation mechanism and is able to adjust an angle of the polarization plane of the linearly polarized light. If the analyzer 11 has a rotation mechanism, the rotation mechanism in the polarizer 9 may be omitted.

The half mirror 10 is an optical path dividing means that guides linearly polarized light transmitted through the polarizer 9 to the magnetooptic element 5 and guides reflected polarized light reflected from the magnetooptic element 5 to the detector 12. The analyzer 11 adjusts polarized light detected by the detector 12 by adjusting a relative angle thereof with the above described polarizer 9. The detector 12 is a general two-dimensional image acquiring device, such as a so-called CCD camera or CMOS camera. An image detected by the detector 12 is subjected to appropriate image processing by a separate image processing means 13, such as a PC.

By an optical element, such as a lens or the like, which is not illustrated in FIG. 2, a luminous flux diameter upon irradiation of the magnetooptic element 5 is adjusted to match a size of the magnetooptic element 5. Further, the optical system from the magnetooptic element 5 to the detector 12 is a telecentric optical system.

Figure 3:
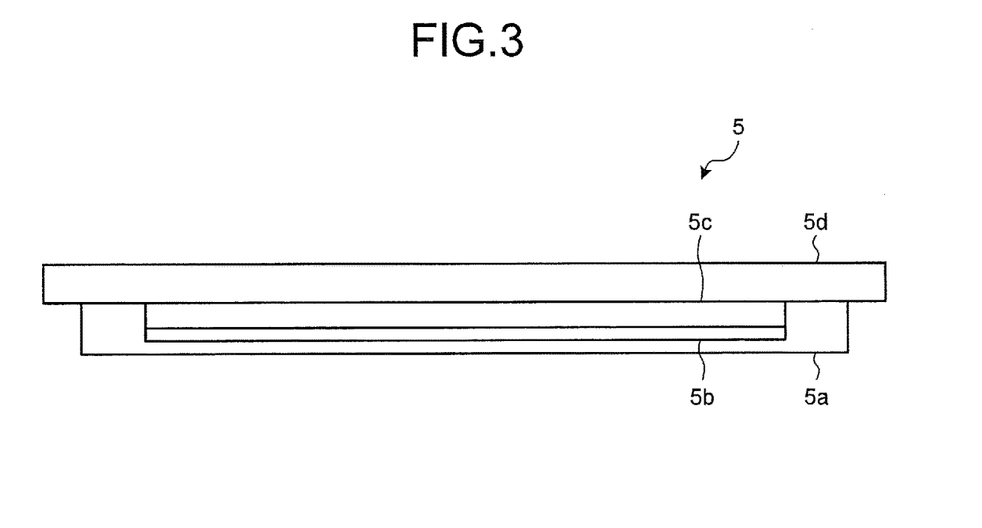
FIG. 3 is a cross section diagram illustrating an example of a configuration of a magnetooptic element.

FIG. 3 is a cross section diagram illustrating an example of a configuration of the magnetooptic element 5. As illustrated in FIG. 3, the magnetooptic element 5 is configured of, in order from a direction facing the steel sheet "S", a protective film 5a, a reflective film 5b, a magnetooptic film 5c, and a substrate 5d. The magnetooptic film 5c preferably has a composition including magnetic garnet. The polarized light, with which this magnetooptic element 5 is irradiated, is incident on the substrate 5d, transmitted through the magnetooptic film 5c, reflected by the reflective film 5b, and thereafter transmitted through the magnetooptic film 5c and the substrate 5d again to be emitted from the magnetooptic element 5.

Figure 4:
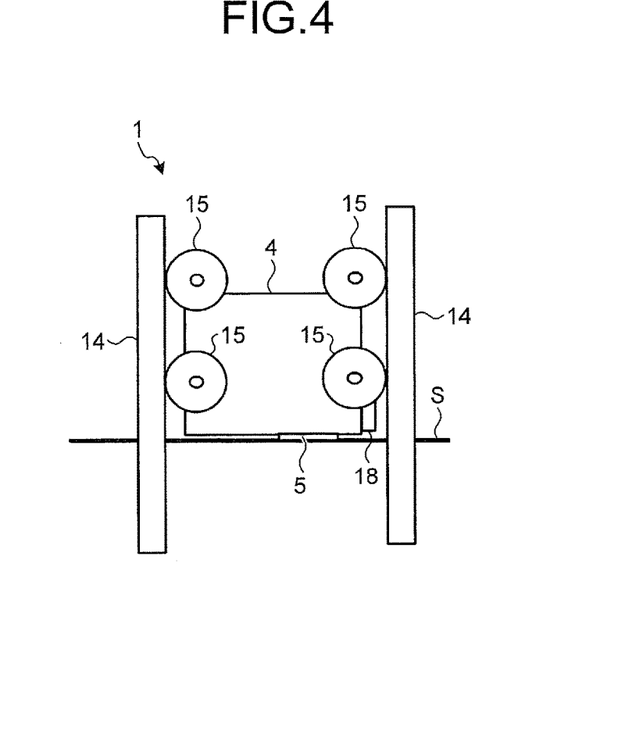
FIG. 4 is a side view of a drive mechanism of the steel sheet inspection device.
Figure 5:
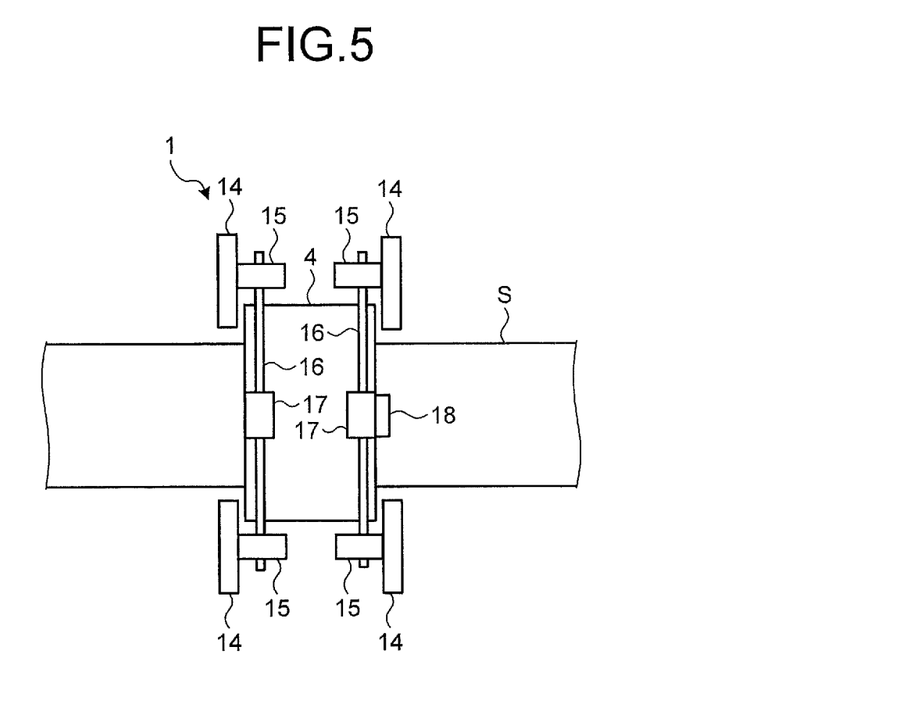
FIG. 5 is a top view of the drive mechanism of the steel sheet inspection device.

FIG. 4 and FIG. 5 are schematic configuration diagrams illustrating a drive system of the steel sheet inspection device 1 according to the embodiment of the present invention. FIG. 4 is a side view of a drive mechanism of the steel sheet inspection device 1 and FIG. 5 is a top view of the drive mechanism of the steel sheet inspection device 1.

As illustrated in FIG. 4 and FIG. 5, in the steel sheet inspection device 1 according to the embodiment of the present invention, the inspection unit 4 is able to move up and down along rails 14 vertically placed on both sides of the manufacturing line of the steel sheet "S". The inspection unit 4 is arranged movably on the rails 14 by wheels 15, and a motor 17 is provided on each of axles 16 of the wheels 15. The inspection unit 4 moves up and down along the rails 14 by rotational drive of the motors 17.

As illustrated in FIG. 4 and FIG. 5, the inspection unit 4 includes a proximity sensor 18. The proximity sensor 18 is a sensor for measuring a distance between the inspection unit 4 and the surface of the steel sheet "S". In the steel sheet inspection device 1 according to the embodiment of the present invention, when the inspection unit 4 is lowered to cause the magnetooptic element 5 to come into contact with the surface of the steel sheet "S", the inspection unit 4 is lowered at a low speed near the steel sheet "S" such that the surface of the steel sheet "S" and the magnetooptic element 5 are not damaged by colliding each other. The proximity sensor 18 detects a height where the lowering speed of the inspection unit 4 is to be changed to the low speed.

The drive mechanism illustrated in FIG. 4 and FIG. 5 is just an example that may be applied to the steel sheet inspection device 1 according to the embodiment of the present invention. Therefore, not being limited to the drive mechanism illustrated in FIG. 4 and FIG. 5, another mechanism, such as that of winch type, may be used. Further, the drive mechanism illustrated in FIG. 4 and FIG. 5 drives the inspection unit 4 integrally therewith, but a configuration, which drives only some of the structural elements included in the inspection unit 4, for example, the magnetooptic element 5 and the holder 6, may be used.

Modified Example

Figure 6:
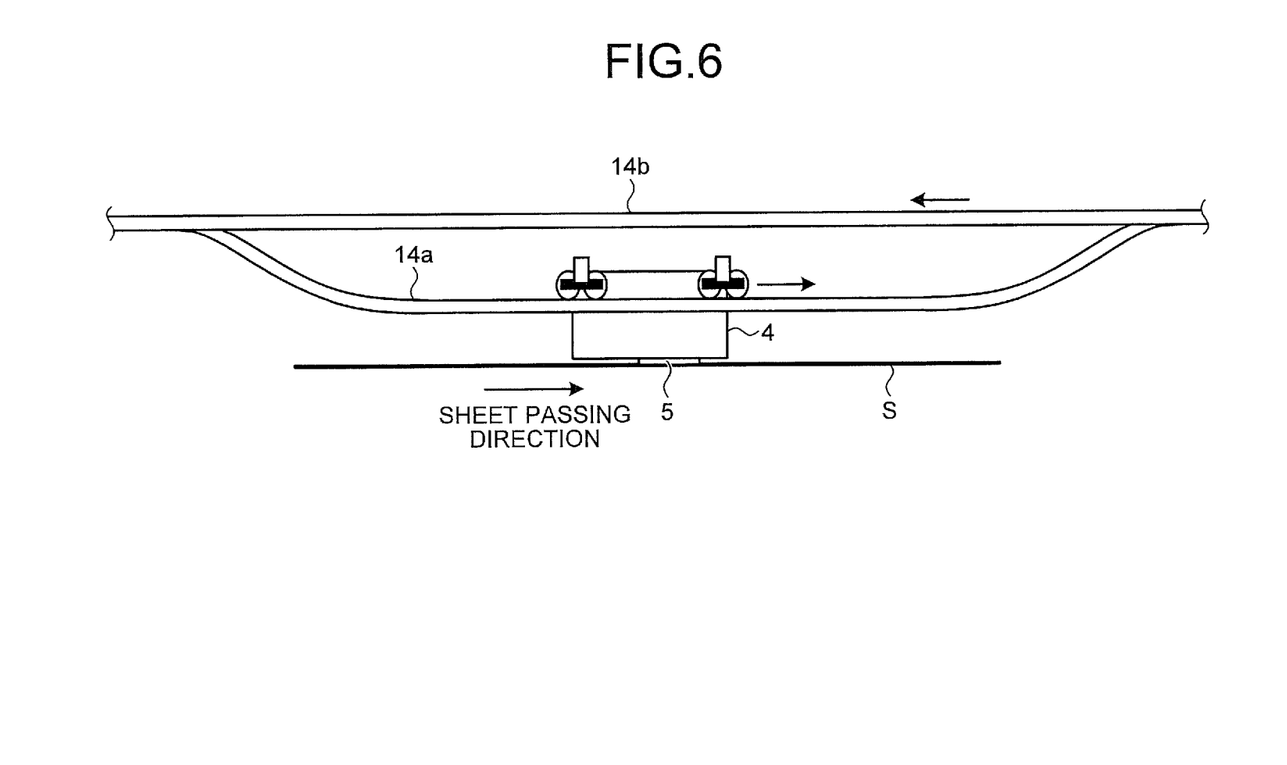
FIG. 6 is a schematic configuration diagram illustrating a modified example of a drive system of the steel sheet inspection device according to the embodiment of the present invention.

FIG. 6 is a schematic configuration diagram illustrating a modified example of the drive system of the steel sheet inspection device 1 according to the embodiment of the present invention. As illustrated in FIG. 6, in this modified example of the drive system of the steel sheet inspection device 1 according to the embodiment of the present invention, the surface of the steel sheet "S" and the magnetooptic element 5 are caused to come into contact with each other while the steel sheet "S" being passed is travelling alongside thereof.

As illustrated in FIG. 6, the inspection unit 4 moves on a rail 14a near the steel sheet "S" and a rail 14b far from the steel sheet "S". When the inspection unit 4 is moving on the rail 14a near the steel sheet "S", the magnetooptic element 5 of the inspection unit 4 comes into contact with the surface of the steel sheet "S" and is brought into a state of being able to inspect the magnetic domain structure of the steel sheet "S". On the contrary, when the inspection unit 4 is moving on the rail 14b far from the steel sheet "S", since the magnetooptic element 5 of the inspection unit 4 does not come into contact with the surface of the steel sheet "S", the inspection unit 4 moves upstream of the sheet's passage for the next inspection.

A method of connecting the rail 14a near the steel sheet "S" with the rail 14b far from the steel sheet "S" may be, as illustrated in FIG. 6, of a switch-over type but an orbiting path may be formed instead. Further, power to move the inspection unit 4 on the rails is supplied by motors provided on axels of the wheels, similarly to the driving method illustrated in FIG. 4 and FIG. 5. An internal configuration of the inspection unit 4 may be similar to the example of the internal configuration of the inspection unit 4 illustrated in FIG. 2.

[Steel Sheet Inspection Method]

Hereinafter, a steel sheet inspection method according to the embodiment of the present invention will be described. In the following description, although the steel sheet inspection method according to the embodiment of the present invention will be described with reference to the drawings of the configuration of the steel sheet inspection device according to the embodiment of the present invention, the steel sheet inspection method according to the embodiment of the present invention is not limited by the configuration illustrated in these drawings.

Figure 7:
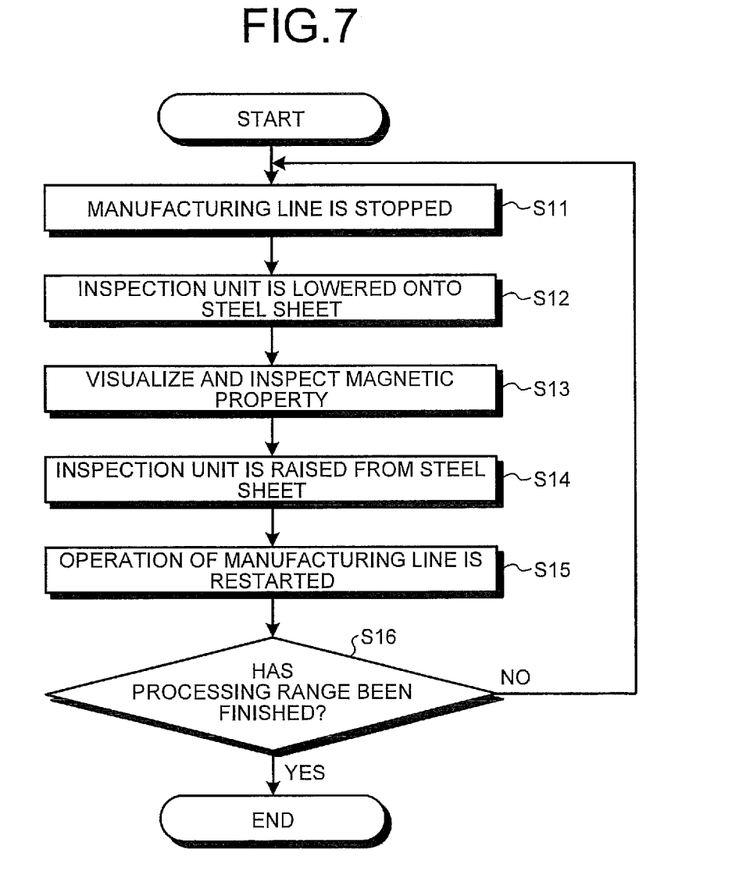
FIG. 7 is a flow chart illustrating a steel sheet inspection method according to the embodiment of the present invention.

FIG. 7 is a flow chart illustrating the steel sheet inspection method according to the embodiment of the present invention. As illustrated in FIG. 7, the steel sheet inspection method according to the embodiment of the present invention is carried out in a state where the manufacturing line of the steel sheet "S" has been stopped (Step S11). However, like the above described modified example of the drive system of the steel sheet inspection device 1, for a steel sheet inspection method in a situation where the manufacturing line of the steel sheet "S" has not been stopped, an embodiment omitting this Step S11 is applicable, too.

Next, the inspection unit 4 of the steel sheet inspection device 1 is lowered towards the surface of the steel sheet "S" (Step S12). By the inspection unit 4 being lowered towards the surface of the steel sheet "S", the magnetooptic element 5 comes into contact with the surface of the steel sheet "S" and the magnetic domain structure of the steel sheet "S" is transferred to the magnetooptic film 5c of the magnetooptic element 5.

Thereafter, the magnetic property (magnetic domain structure) of the steel sheet "S" is visualized and inspected (Step S13). That is, by the magnetooptic element 5 being irradiated with the linearly polarized light, and the linearly polarized light passing through the magnetooptic film 5c of the magnetooptic element 5, rotation of the polarization plane due to Faraday effect occurs, and the inspection unit 4 performs visualization and inspection of the magnetic domain structure of the steel sheet "S" by this rotation of the polarization plane.

The visualized magnetic domain structure of the steel sheet "S" is subjected to appropriate image processing by a separate image processing means 13, such as a PC. The image processing means 13 performs magnetic domain discontinuity evaluation and detects a boundary between a magnetic domain and a magnetic domain discontinuity, for a visualized image of the magnetic domain structure of the steel sheet "S". Further, the image processing means 13 calculates a width of the magnetic domain discontinuity, based on the size of the magnetooptic element 5, a magnification of the measurement optical system, the distance to the steel sheet "S", and the like, and checks whether the width is equal to a predetermined width.

Thereafter, the inspection unit 4 of the steel sheet inspection device 1 is raised from the surface of the steel sheet "S" (Step S14), and the magnetooptic element 5 is separated from the surface of the steel sheet "S". Operation of the manufacturing line of the steel sheet "S" is then restarted (Step S15).

Lastly, determination of whether or not a processing range of the magnetic domain refining process on the steel sheet "S" has been finished is performed (Step S16), and if not finished (Step S16; No), the process from Step S11 to Step S15 is repeated. On the contrary, if the processing range of the magnetic domain refining process on the steel sheet "S" has been finished (Step S16; Yes), inspection of the steel sheet is ended. If the steel sheet inspection method according to the embodiment of the present invention is actually carried out, the process from Step S11 to Step S15 takes about one second.

Figure 8:
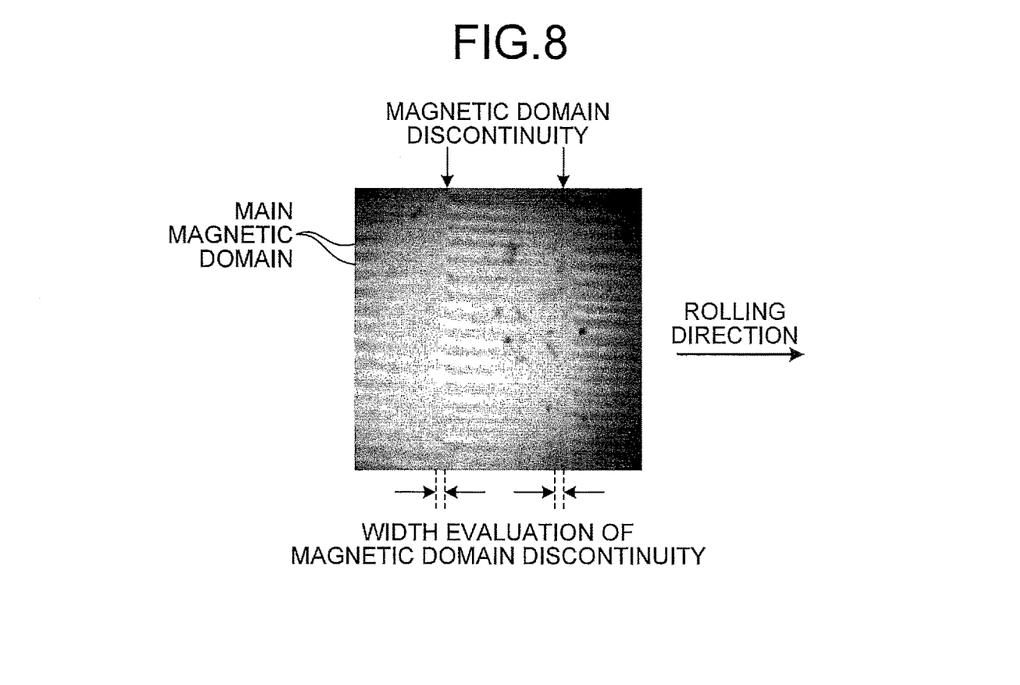
FIG. 8 is an image illustrating an example of an inspection image of a grain oriented electrical steel sheet by the steel sheet inspection device and the steel sheet inspection method according to the embodiment of the present invention.

FIG. 8 is an image illustrating an example of an inspection image of a grain oriented electrical steel sheet by the steel sheet inspection device 1 and the steel sheet inspection method according to the embodiment of the present invention. The image illustrated in FIG. 8 is a cut-out of 10 mm in the rolling direction×10 mm in the sheet width direction from the inspection image of the grain oriented electrical steel sheet.

Upon acquirement of the image illustrated in FIG. 8, iron garnet substituted with Bi, which is an example of magnetic garnet, is used as the magnetooptic film 5c in the magnetooptic element 5. In order to make Faraday effect due to magnetic garnet easy to be visually recognized, as the light source 7, a green LED light source (wavelength of 505 nm) in combination with a polarizing filter were used, and a CCD camera was used as the detector 12.

As illustrated in FIG. 8, in the grain oriented electrical steel sheet, at a portion irradiated with the electron beams or laser, a closure domain (hereinafter, magnetic domain discontinuity) dividing a main magnetic domain along the rolling direction is formed. The width of the magnetic domain discontinuity is known to have good correlation with the core loss. From FIG. 8, it is understood that a magnetic domain discontinuity has a magnetic property different from that of a surrounding magnetic domain thereof, and that by using the steel sheet inspection device 1 and the steel sheet inspection method according to the embodiment of the present invention, measurement of the width of a magnetic domain discontinuity is possible.

There are experimental results indicating that if the width of the magnetic domain discontinuity is 150 μm to 300 μm, the core loss of the steel sheet is reduced (for example, see Japanese Patent Application Laid-open No. 2012-052230).

Further, the smaller the width of the refined magnetic domain, the shorter the moving distance of the magnetic domain wall upon magnetic excitation will be and the smaller the loss accompanying this will be, and for example, the width of a magnetic domain is preferably equal to or less than 200 μm. When the width of such a magnetic domain discontinuity or the width of a magnetic domain is evaluated, each width may be measured, but in general, evaluation is performed with an average value measured for a certain section. It is understood that the width of the magnetic domain discontinuity illustrated in FIG. 8 is approximately 200 μm, and it is understood that the magnetic domain discontinuity within a proper range has been formed. Accordingly, by using the steel sheet inspection device 1 and the steel sheet inspection method according to the embodiment of the present invention, quality evaluation of the steel sheet "S" is possible.

[Steel Sheet Manufacturing Method]

Next, a steel sheet manufacturing method according to the embodiment of the present invention will be described.

Figure 9:
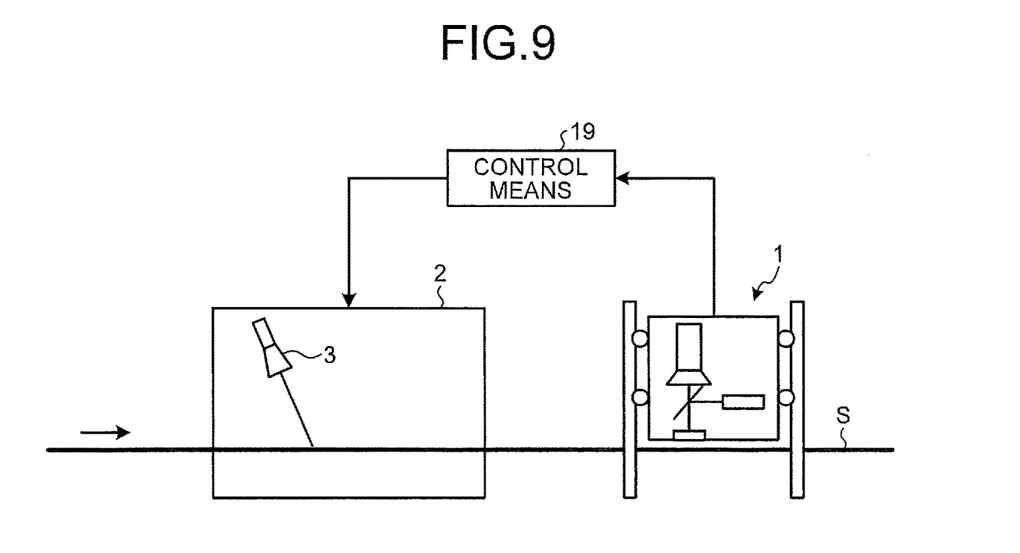
FIG. 9 is a configuration diagram illustrating a manufacturing line including the steel sheet inspection device according to the embodiment of the present invention.

FIG. 9 is a configuration diagram illustrating a manufacturing line including the steel sheet inspection device 1 according to the embodiment of the present invention. As illustrated in FIG. 9, the steel sheet inspection device 1 according to the embodiment of the present invention is arranged at the rear stage of the magnetic domain refining device 2 that performs the magnetic domain refining process on the steel sheet "S". The magnetic domain refining device 2 includes the electron guns 3 therein, and is the device that gives the thermal strain in the direction intersecting a magnetic domain of the steel sheet "S" by irradiating the steel sheet "S" with the electron beams from the electron guns 3.

The magnetic domain refining device 2 performs the magnetic domain refining process on the surface of the steel sheet "S" and the steel sheet inspection device 1 inspects the surface of the steel sheet "S" subjected to the magnetic domain refining process by the magnetic domain refining device 2. Based on a result of the inspection by the steel sheet inspection device 1, a control means 19 controls the magnetic domain refining device 2. The control means 19 may be an automatic control device, such as a PLC, or manual control by an operator.

Figure 10:
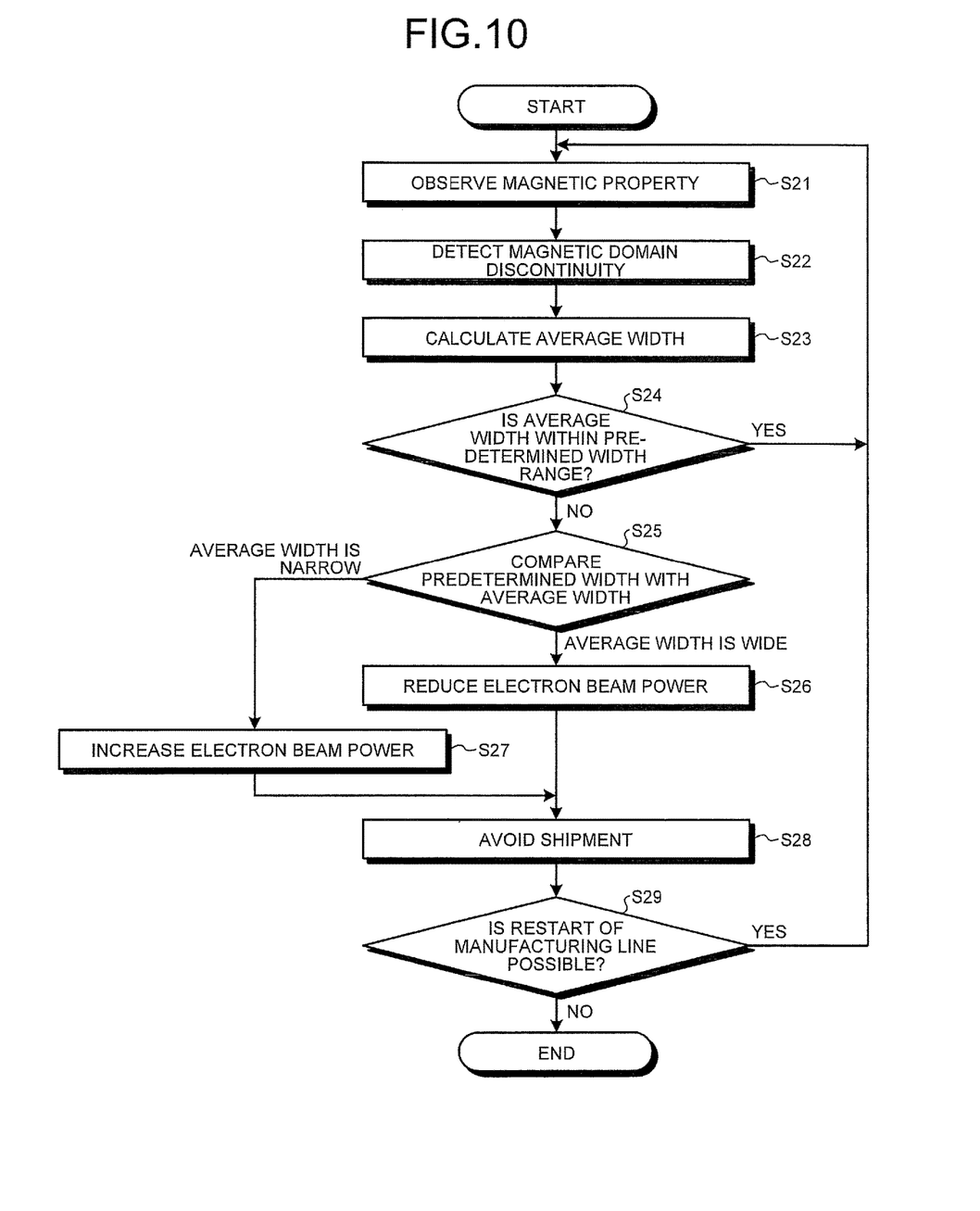
FIG. 10 is a flow chart illustrating a steel sheet manufacturing method according to the embodiment of the present invention.

FIG. 10 is a flow chart illustrating the steel sheet manufacturing method according to the embodiment of the present invention. As illustrated in FIG. 10, in the steel sheet manufacturing method according to the embodiment of the present invention, first, a magnetic property (magnetic domain structure) of the steel sheet "S" subjected to the magnetic domain refining process by the magnetic domain refining device 2 is visualized and inspected by the steel sheet inspection device 1 (Step S21).

The image processing means 13 of the steel sheet inspection device 1 then performs the magnetic domain discontinuity evaluation on a visualized image of the magnetic domain structure of the steel sheet "S" and detects a boundary between a magnetic domain and a magnetic domain discontinuity (Step S22). Further, the image processing means 13 of the steel sheet inspection device 1 calculates an average width of a magnetic domain discontinuity included in a predetermined range, based on the size of the magnetooptic element 5, the magnification of the measurement optical system, the distance to the steel sheet "S", and the like (Step S23).

Thereafter, the control means 19 evaluates the average width of the magnetic domain discontinuity and determines whether or not the average width is within a predetermined width range (Step S24). If the average width is within a predetermined width range (Step S24; Yes), the magnetic domain refining process has been performed properly and thus in order to continue manufacturing the steel sheet "S", the control means 19 returns to Step S21. On the contrary, if the average width is not within the predetermined range (Step S24; No), the average width and a predetermined width are compared to each other (Step S25).

If the average width is wider than the predetermined value (Step S25; average width is wide), the control means 19 issues an order to reduce an electron beam power of the electron guns 3 of the magnetic domain refining device 2 (Step S26) and avoids shipment of the steel sheet "S" that has been subjected to the magnetic domain refining process under the same conditions already (Step S28). On the contrary, if the average width is narrower than the predetermined value (Step S25; average width is narrow), the control means 19 issues an order to increase an electron beam power of the electron guns 3 of the magnetic domain refining device 2 (Step S27) and avoids the shipment of the steel sheet "S" that has been subjected to the magnetic domain refining process under the same conditions already.

Thereafter, the control means 19 determines whether or not continuing operation (restart) of the manufacturing line of the steel sheet "S" is possible (Step S29). That is, a factor causing the deviation of the average width of the magnetic domain discontinuity from the predetermined width range may be that due to the life of a filament of the electron guns 3, due to occurrence of a problem in the device, or the like. Therefore, the control means 19 determines whether or not the continuing operation of the manufacturing line is possible based on the factor causing the deviation of the average width of the magnetic domain discontinuity from the predetermined width range, and if the continuing operation is possible (Step S29; Yes), returns to Step S21 to continue manufacturing the steel sheet "S". On the contrary, if the continuing operation is not possible (Step S29; No), in order to perform changing of a filament of the electron guns 3 or the like, the manufacturing line is stopped.

Because the steel sheet inspection device 1 according to the embodiment of the present invention includes the magnetooptic element 5 that is able to detect the magnetic domain structure of the steel sheet "S" to be inspected as the optical property, the light source that irradiates the magnetooptic element 5 with the linearly polarized light, the detector 12 that detects the linearly polarized light with the polarization plane being rotated according to the magnetic domain structure of the steel sheet "S" transferred to the magnetooptic element 5, and the drive mechanism that drives at least the magnetooptic element 5 to contact and separate the steel sheet "S" and the magnetooptic element 5 with and from each other, by visualizing and inspecting the magnetic domain structure of the steel sheet "S" immediately after the magnetic domain refining process, the yield is able to be improved.

Further, because the magnetooptic element 5 according to the embodiment of the present invention is configured of, in the order from the direction facing the steel sheet "S", the protective film 5a, the reflective film 5b, the magnetooptic film 5c, and the substrate 5d, and the linearly polarized light is incident from the substrate 5d side and reflected by the reflective film 5b, by the incident linearly polarized light traveling back and forth through the magnetooptic film 5c, Faraday effect is able to be doubly obtained. Moreover, the magnetooptic film 5c preferably has the composition including magnetic garnet.

INDUSTRIAL APPLICABILITY

As described above, a steel sheet inspection device, a steel sheet inspection method, and a steel sheet manufacturing method according to the present invention are applicable to a process of visualizing and inspecting a magnetic domain structure of a steel sheet immediately after a magnetic domain refining process thereon.

REFERENCE SIGNS LIST

1 Steel sheet inspection device
2 Magnetic domain refining device
3 Electron gun
4 Inspection unit
5 Magnetooptic element
5a Protective film
5b Reflective film
5c Magnetooptic film
5d Substrate
6 Holder
7 Light source
8 Collimator lens
9 Polarizer
10 Half mirror
11 Analyzer
12 Detector
13 Image processing means
14, 14a, 14b Rail
15 Wheel
16 Axle
17 Motor
18 Proximity sensor
19 Control means

The invention claimed is:

1. A steel sheet inspection device, comprising:
a magnetooptic element that is able to detect, as an optical property, a magnetic domain structure of a steel sheet to be inspected;
a light source that irradiates the magnetooptic element with linearly polarized light;
a detector that detects the linearly polarized light with a polarization plane rotated according to the magnetic domain structure of the steel sheet transferred to the magnetooptic element; and
a drive mechanism that drives an inspection unit accommodating at least the magnetooptic element so as to contact and separate the steel sheet and the magnetooptic element with and from each other, the drive mechanism being configured to move the inspection unit on a rail near the steel sheet or on a rail far from the steel sheet and configured to bring the magnetooptic element into contact with a surface of the steel sheet while the steel sheet being passed is traveling alongside the inspection unit by moving the inspection unit on the rail near the steel sheet.

2. The steel sheet inspection device according to claim 1, wherein
the magnetooptic element is configured of, in order from a direction facing the steel sheet, a protective film, a reflective film, a magnetooptic film, and a substrate, and
the linearly polarized light is incident from a side of the substrate and is reflected by the reflective film.

3. The steel sheet inspection device according to claim 2, wherein the magnetooptic film has a composition including magnetic garnet.

4. The steel sheet inspection device according to claim 1, further comprising a polarizer, a half mirror, and an analyzer, wherein a light ray emitted from the light source is propagated through and in the order of, the polarizer, the half mirror, the magnetooptic element, the half mirror, the analyzer, and the detector.

5. The steel sheet inspection device according to claim 4, wherein the drive mechanism contacts and separates the steel sheet and the magnetooptic element with and from each other by driving the inspection unit accommodating therein the light source, the polarizer, the half mirror, the magnetooptic element, the analyzer, and the detector.

6. The steel sheet inspection device according to claim 5, wherein the magnetooptic element is fixed to the inspection unit via an elastic body.

7. A steel sheet inspection method, comprising:
  a contacting step of contacting, with a steel sheet to be inspected, a magnetooptic element that is able to detect, as an optical property, a magnetic domain structure of the steel sheet;
  an irradiating step of irradiating the magnetooptic element with linearly polarized light;
  a detecting step of detecting a rotation of a polarization plane of the linearly polarized light reflected by the magnetooptic element;
  a measuring step of measuring the magnetic domain structure of the steel sheet from the rotation of the polarization plane; and
  a separating step of separating the magnetooptic element from the steel sheet,
  wherein the contacting step, by using a drive mechanism configured to move an inspection unit accommodating at least the magnetooptic element on a rail near the steel sheet or on a rail far from the steel sheet, brings the magnetooptic element into contact with a surface of the steel sheet while the steel sheet being passed is traveling alongside the inspection unit by moving the inspection unit on the rail near the steel sheet.

8. The steel sheet inspection method according to claim 7, wherein
  the magnetooptic element is configured of, in order from a direction facing the steel sheet, a protective film, a reflective film, a magnetooptic film, and a substrate, and
  the linearly polarized light is incident from a side of the substrate and is reflected by the reflective film.

9. The steel sheet inspection method according to claim 8, wherein the magnetooptic film has a composition including magnetic garnet.

10. A method of manufacturing a grain oriented electrical steel sheet, the method comprising:
  a magnetic domain refining step of irradiating a surface of a steel sheet with an electron beam or laser;
  a contacting step of contacting a magnetooptic element that is able to detect, as an optical property, a magnetic domain structure of a steel sheet, with a region on the steel sheet, the region having been irradiated with the electron beam or laser;
  an irradiating step of irradiating the magnetooptic element with linearly polarized light;
  a detecting step of detecting a rotation of a polarization plane of the linearly polarized light reflected by the magnetooptic element;
  an extracting step of extracting a magnetic domain discontinuity formed by the irradiation with the electron beam or laser;
  a width evaluating step of evaluating an average width of the magnetic domain discontinuity;
  an output adjusting step of increasing or decreasing an output of the electron beam or laser when the width evaluating step has evaluated that the average width is not within a predetermined range; and
  when the width evaluating step has evaluated that the average width is within a predetermined range, forming a manufactured steel sheet,
  wherein the contacting step, by using a drive mechanism configured to move an inspection unit accommodating at least the magnetooptic element on a first rail near the steel sheet or on a second rail far from the steel sheet, brings the magnetooptic element into contact with a surface of the steel sheet while the steel sheet being passed is traveling alongside the inspection unit by moving the inspection unit on the first rail.

11. The method of manufacturing a grain oriented electrical steel sheet according to claim 10, further comprising:
  a shipment step of shipping the steel sheet that has been manufactured; and
  a shipment avoiding step of causing the shipment step to avoid shipment of the steel sheet that has been manufactured before the output adjusting step has increased or decreased the output of the electron beam or laser when the width evaluating step has evaluated that the average width is not within a predetermined range.

12. The method of manufacturing a grain oriented electrical steel sheet according to claim 10, wherein
  the magnetooptic element is configured of, in order from a direction facing the steel sheet, a protective film, a reflective film, a magnetooptic film, and a substrate, and
  the linearly polarized light is incident from a side of the substrate and is reflected by the reflective film.

13. The method of manufacturing a grain oriented electrical steel sheet according to claim 12, wherein the magnetooptic film has a composition including magnetic garnet.

14. The steel sheet inspection device according to claim 2, further comprising a polarizer, a half mirror, and an analyzer, wherein a light ray emitted from the light source is propagated through and in the order of, the polarizer, the half mirror, the magnetooptic element, the half mirror, the analyzer, and the detector.

15. The steel sheet inspection device according to claim 14, wherein the drive mechanism contacts and separates the steel sheet and the magnetooptic element with and from each other by driving the inspection unit accommodating therein the light source, the polarizer, the half mirror, the magnetooptic element, the analyzer, and the detector.

16. The steel sheet inspection device according to claim 15, wherein the magnetooptic element is fixed to the inspection unit via an elastic body.

17. The steel sheet inspection device according to claim 3, further comprising a polarizer, a half mirror, and an analyzer, wherein a light ray emitted from the light source is propagated through and in the order of, the polarizer, the half mirror, the magnetooptic element, the half mirror, the analyzer, and the detector.

18. The steel sheet inspection device according to claim 17, wherein the drive mechanism contacts and separates the steel sheet and the magnetooptic element with and from each other by driving the inspection unit accommodating therein the light source, the polarizer, the half mirror, the magnetooptic element, the analyzer, and the detector.

19. The steel sheet inspection device according to claim 18, wherein the magnetooptic element is fixed to the inspection unit via an elastic body.

20. The method of manufacturing a grain oriented electrical steel sheet according to claim 11, wherein the magnetooptic element is configured of, in order from a direction facing the steel sheet, a protective film, a reflective film, a magnetooptic film, and a substrate, and the linearly polarized light is incident from a side of the substrate and is reflected by the reflective film.

* * * * *